(12) United States Patent
Graham

(10) Patent No.: US 9,675,779 B2
(45) Date of Patent: Jun. 13, 2017

(54) HEMODIALYSIS WAND HOLDER AND ASSOCIATED USE THEREFORE

(71) Applicant: Virginia Graham, Rosemead, CA (US)

(72) Inventor: Virginia Graham, Rosemead, CA (US)

( * ) Notice: Subject to any disclaimer, the term of this patent is extended or adjusted under 35 U.S.C. 154(b) by 241 days.

(21) Appl. No.: 14/752,691

(22) Filed: Jun. 26, 2015

(65) Prior Publication Data

US 2016/0375191 A1 Dec. 29, 2016

(51) Int. Cl.
*B65D 83/10* (2006.01)
*A61M 25/00* (2006.01)
*A61M 1/36* (2006.01)
*A61M 1/16* (2006.01)

(52) U.S. Cl.
CPC ........ *A61M 25/002* (2013.01); *A61M 1/1656* (2013.01); *A61M 1/3661* (2014.02); *A61M 2205/11* (2013.01); *A61M 2209/06* (2013.01); *A61M 2209/082* (2013.01); *A61M 2209/084* (2013.01)

(58) Field of Classification Search
CPC .............. A61M 1/3661; A61M 25/002; A61M 2209/06; A61M 2209/082; A61M 2209/086
USPC ....... 206/204, 363, 364, 368, 369, 370, 499; 53/400, 452, 468, 473; 604/6.16
See application file for complete search history.

(56) References Cited

U.S. PATENT DOCUMENTS

| | | | | |
|---|---|---|---|---|
| 6,053,314 A | * | 4/2000 | Pittman | A61M 5/3205 206/366 |
| 6,286,678 B1 | * | 9/2001 | Petrek | B01L 9/543 206/443 |
| 7,431,157 B2 | * | 10/2008 | Porret | A61L 2/08 206/363 |
| 7,694,822 B2 | * | 4/2010 | Sullivan | A61B 17/3217 206/366 |
| 8,056,719 B2 | * | 11/2011 | Porret | A61K 47/48084 206/370 |
| 2005/0109662 A1 | * | 5/2005 | Kirk | A47K 1/09 206/210 |
| 2013/0186793 A1 | * | 7/2013 | Gagnieux | A61M 5/002 206/364 |
| 2015/0078961 A1 | * | 3/2015 | Opie | A61L 2/26 206/370 |
| 2015/0291352 A1 | * | 10/2015 | Morgan | A61M 1/0017 588/252 |

* cited by examiner

*Primary Examiner* — Luan K Bui
(74) *Attorney, Agent, or Firm* — Virginia Eugenia Graham

(57) ABSTRACT

A hemodialysis wand holder includes a container having a plurality of side walls configured to form an open top end and a cavity extending downwardly from the open top end. A lid is removably coupled to the open top end wherein the lid has at least one aperture formed therein. At least one hemodialysis wand is removably inserted through the at least one aperture such that the at least one hemodialysis wand is suspended above a bottom one of the side walls. A collection tray is adjustably situated along the bottom side wall. Such a collection tray is removably reciprocated along a linear travel path registered transverse to a front one of the side walls. A fluid-absorbent liner is removably positioned within the collection tray for receiving fluids dripping down from the at least one hemodialysis wand suspended partially within the cavity.

15 Claims, 5 Drawing Sheets

HEMODIALYSIS WAND HOLDER AND ASSOCIATED USE THEREFORE

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

Exemplary embodiment(s) of the present disclosure relate to sanitary containers and, more particularly, to a hemodialysis wand holder for providing healthcare workers with a convenient means of storing hemodialysis pickup wands in a sanitary environment prior to use thereof.

Prior Art

In a patient suffering from temporary or permanent kidney failure, cleansing of the blood can be done with an artificial kidney machine; this is known as hemodialysis. Two plastic tubes, one connected to an artery and one to a vein, are implanted in the patient's arm or leg. During dialysis, which can take three to five hours per treatment, blood from the artery tube enters the machine and comes into contact with a thin membrane. Wastes from the blood pass through the membrane into circulating fluid on the other side of the membrane. The blood cells themselves cannot cross the membrane. The cleaned blood is then piped back into the patient through the vein tube.

In dialysis, a hemodialysis solution is prepared and passed through a dialyzer to extract contaminants from a patient's blood. Moreover, the dialyzer is disinfected prior to a treatment. It is known to produce the hemodialysis solution by dissolving a powder in water within the dialyzer by flowing water through a cartridge containing the powder. Generally, the powder is sodium bicarbonate. Thus, a liquid concentrate is prepared that will later be diluted with water to obtain the concentration required for hemodialysis. A dialysis pickup wand is also employed during hemodialysis. Currently, there is no convenient means of holding such wands in an organized and sanitary way.

Accordingly, a need remains for a sanitary container for hemodialysis wands and the like in order to overcome the above-noted shortcomings. The present invention satisfies such a need by providing an assembly that is convenient and easy to use, is durable yet lightweight in design, is versatile in its applications, and provides a more hygienic and safer way to keep dialysis wands readily available for use after they have been rinsed with de-ionized water than the impromptu methods that are currently used by dialysis centers and clinics

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a hemodialysis wand holder for maintaining hemodialysis wands in a sanitary environment after being used and rinsed with deionized water. These and other objects, features, and advantages of the non-limiting exemplary embodiment(s) are provided by a hemodialysis wand holder including a container having a plurality of side walls configured to form an open top end and a cavity extending downwardly from the open top end. A lid is removably coupled to the open top end wherein the lid has at least one aperture formed therein. At least one hemodialysis wand is removably inserted through the at least one aperture such that the at least one hemodialysis wand is suspended above a bottom one of the side walls. A collection tray is adjustably situated along the bottom side wall. Such a collection tray is removably reciprocated along a linear travel path registered transverse to a front one of the side walls. Notably, the collection tray spans across a major surface area of the bottom side wall. A fluid-absorbent liner is removably positioned within the collection tray for receiving fluids dripping down from the at least one hemodialysis wand suspended partially within the cavity.

In a non-limiting exemplary embodiment, the at least one hemodialysis wand includes an upper section including a cylindrical portion and a conical portion attached thereto, and a lower section engaged with the upper section. Such a lower section includes a linear rod attached to the conical portion and extends away therefrom.

In a non-limiting exemplary embodiment, the linear rod has a distal end seated above the collection tray while the upper section is supported above the lid.

In a non-limiting exemplary embodiment, the at least one aperture includes a first row of apertures aligned parallel to a first longitudinal edge of the lid, and a second row of apertures aligned parallel to a second longitudinal edge of the lid. In this manner, the first row of apertures is juxtaposed parallel to the second row of apertures.

In a non-limiting exemplary embodiment, the at least one hemodialysis wand includes a first group of hemodialysis wands removably inserted through the first row of apertures, respectively, and a second group of hemodialysis wands removably inserted through the second row of apertures, respectively. Advantageously, each hemodialysis wand in each of the first group of hemodialysis wands remains spaced apart from each hemodialysis wand of the second group of hemodialysis wands.

In a non-limiting exemplary embodiment, the front side wall includes a linear slot spanning along an entire longitudinal length of the bottom side wall. Such a linear slot is positioned at a distal edge of the front side wall such that the collection tray reciprocates parallel to the bottom side wall and thereby remains spaced subjacent to the at least one hemodialysis wand.

In a non-limiting exemplary embodiment, the collection tray further includes a handle disposed exterior of the cavity when the collection tray is at a fully inserted position within the container.

The present disclosure further includes a method of utilizing a hemodialysis wand holder for maintaining hemodialysis wands in a sanitary environment after being used and rinsed with deionized water. Such a method includes the steps of: obtaining a container having a plurality of side walls configured to form an open top end and a cavity extending downwardly from the open top end; obtaining and removably coupling a lid to the open top end wherein the lid has at least one aperture formed therein; and obtaining and removably inserting at least one hemodialysis wand through the at least one aperture such that the at least one hemodialysis wand is suspended above a bottom one of the side walls.

The method further includes the steps of: obtaining and adjustably situating a collection tray along the bottom side wall such that the collection tray spans across a major surface area of the bottom side wall; obtaining and removably positioning a fluid-absorbent liner within the collection tray for receiving fluids dripping down from the at least one hemodialysis wand suspended partially within the cavity; and removably reciprocating the collection tray along a linear travel path registered transverse to a front one of the side walls.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Figure 1:
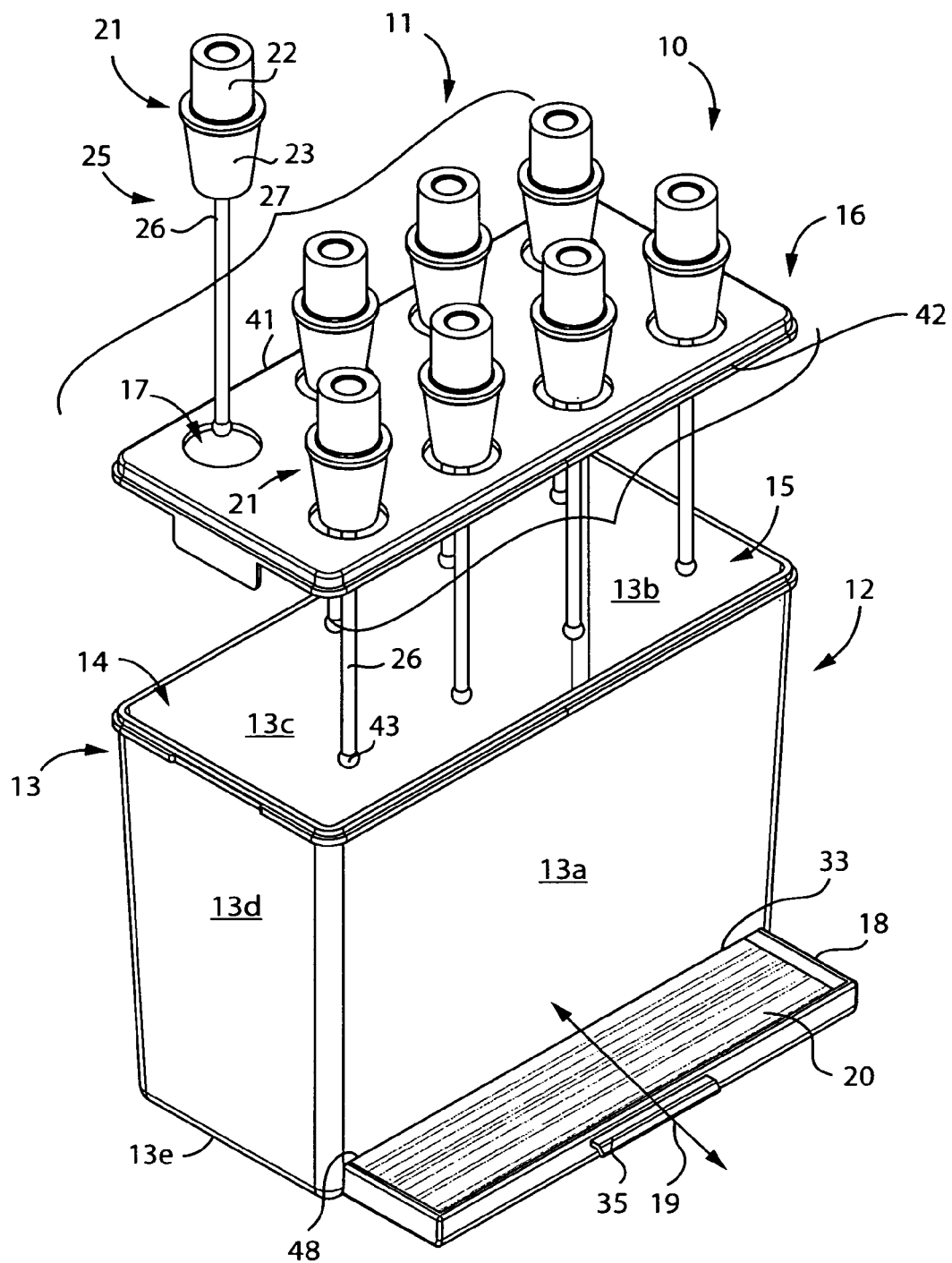
FIG. 1 is an exploded view of a hemodialysis wand holder, in accordance with a non-limiting exemplary embodiment.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary emboidment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

Figure 2:
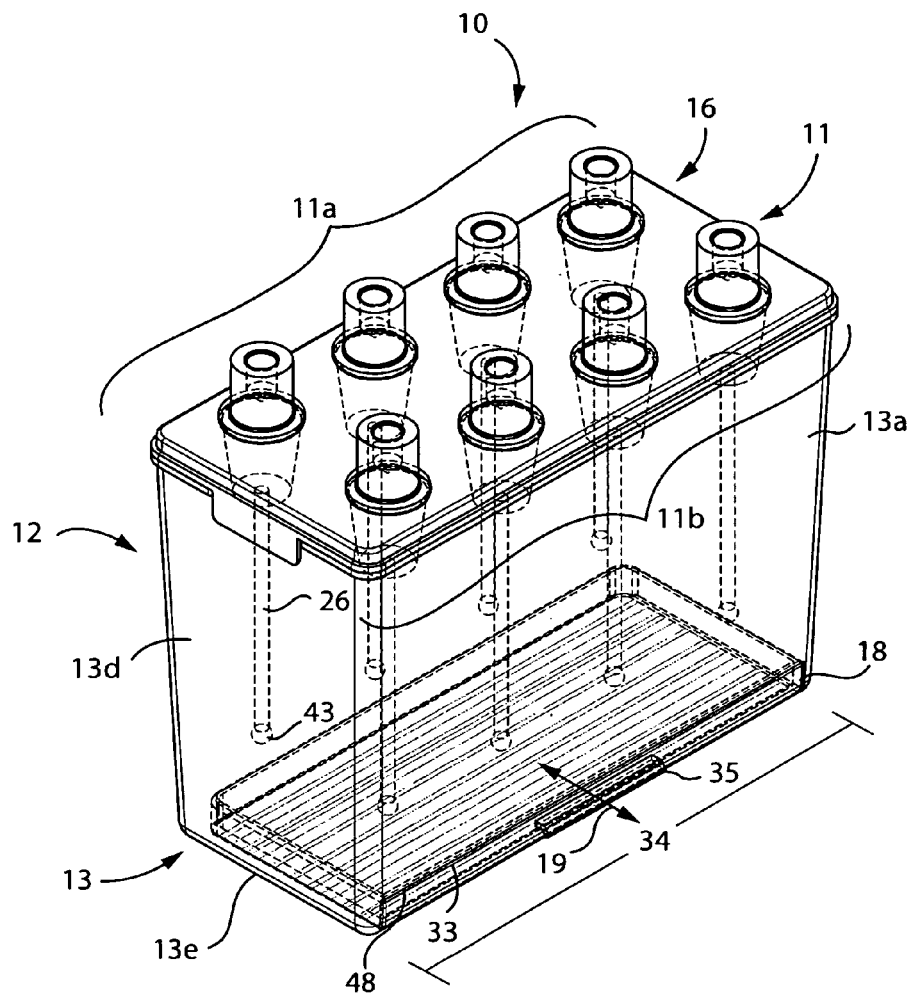
FIG. 2 is a perspective view of the hemodialysis wand holder shown in FIG. 1, wherein the distal ends of each wand is suspended above the collection tray at the bottom of the container.
Figure 3:
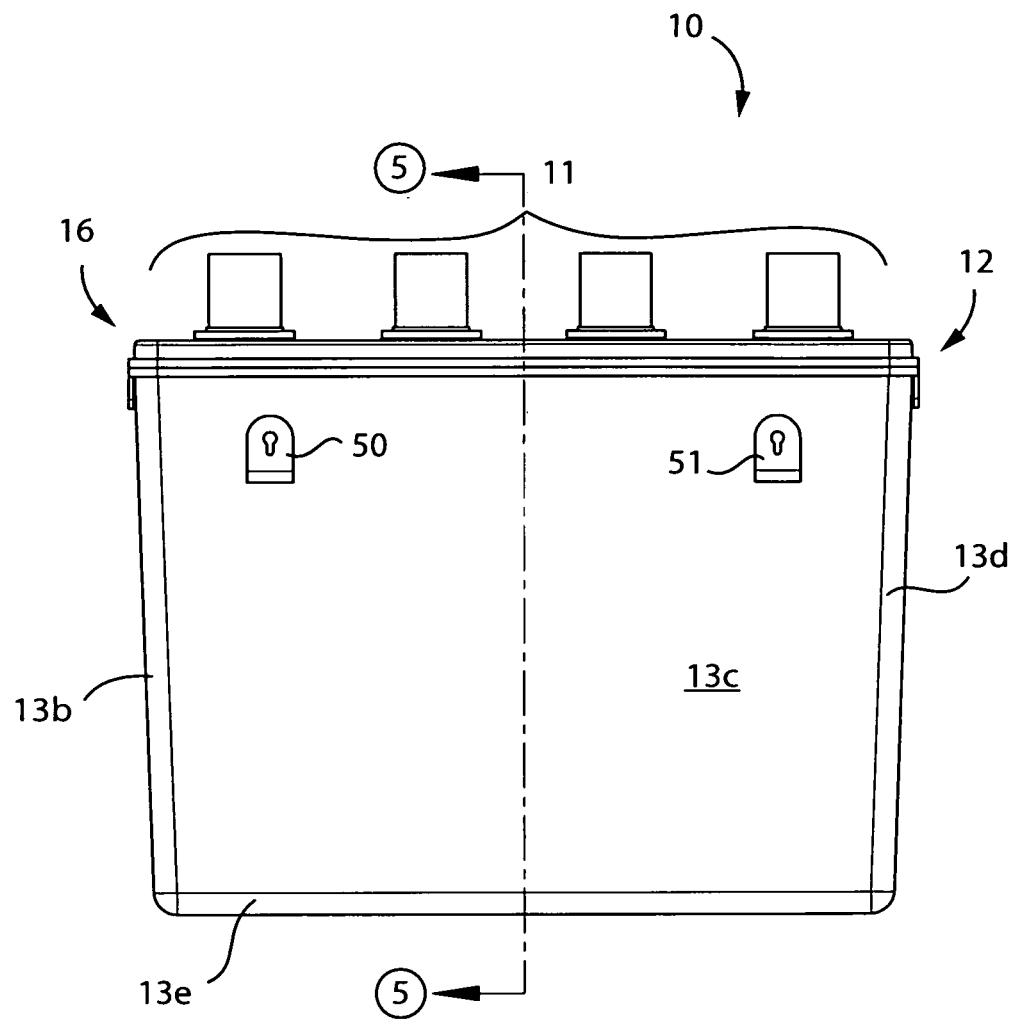
FIG. 3 is a rear elevational view of the hemodialysis wand holder shown in FIG. 2.
Figure 4:
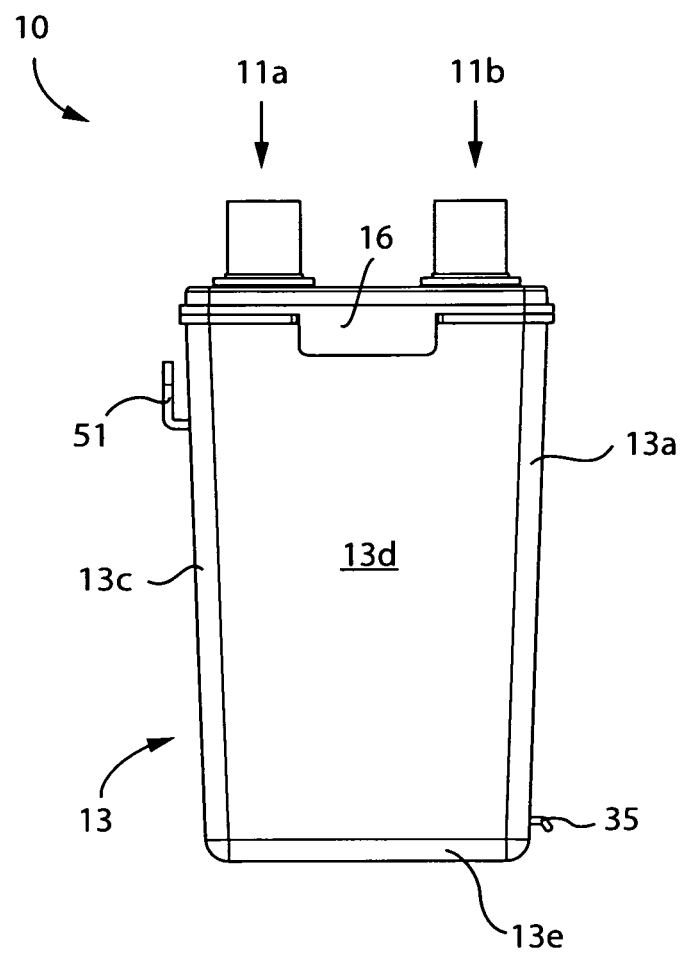
FIG. 4 is a side elevational view of the hemodialysis wand holder shown in FIG. 2.
Figure 5:
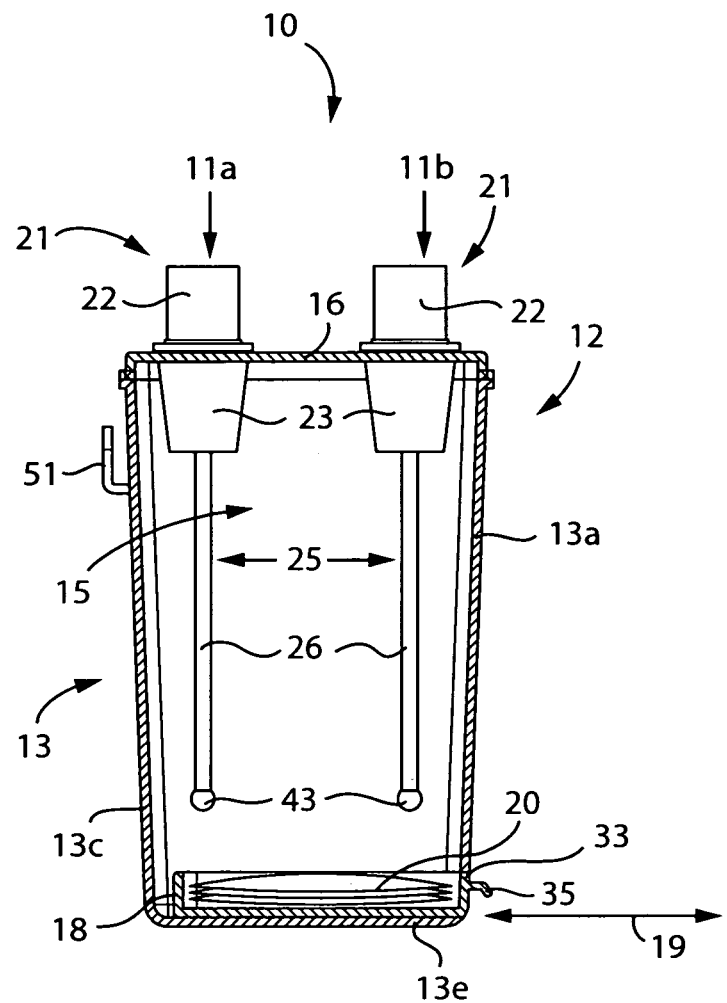
FIG. 5 is a cross-sectional view taken along line 5-5 in FIG. 3.

The non-limiting exemplary embodiment(s) is/are referred to generally in FIGS. 1-5 and is/are intended to provide a hemodialysis wand holder 10 for maintaining hemodialysis wands 11 in a sanitary environment after being used and rinsed with deionized water. Such a hemodialysis wand holder 10 includes a container 12 having a plurality of side walls 13 (e.g., 13a, 13b, 13c, 13d, 13e) configured to form an open top end 14 and a cavity 15 extending downwardly from the open top end 14. A lid 16 is removably coupled to the open top end 14 wherein the lid 16 has at least one aperture 17 formed therein. The at least one hemodialysis wand 11 is removably inserted through the at least one aperture 17 such that the at least one hemodialysis wand 11 is suspended above a bottom one 13e of the side walls 13.

A collection tray 18 is adjustably situated along the bottom side wall 13e. Such a collection tray 18 is removably reciprocated along a linear travel path 19 registered transverse to a front one 13a of the side walls 13. Notably, the collection tray 18 spans across a major surface area of the bottom side wall 13e. A fluid-absorbent liner 20 is removably positioned within the collection tray 18 for receiving fluids dripping down from the at least one hemodialysis wand 11 suspended partially within the cavity 15.

In a non-limiting exemplary embodiment, the at least one hemodialysis wand 11 includes an upper section 21 including a cylindrical portion 22 and a conical portion 23 attached thereto. A lower section 25 is engaged with the upper section 21. Such a lower section 25 includes a linear rod 26 attached to the conical portion 23 and extends away therefrom.

In a non-limiting exemplary embodiment, the linear rod 26 has a distal end 43 seated above the collection tray 18 while the upper section 21 is supported above the lid 16.

In a non-limiting exemplary embodiment, the at least one aperture 17 includes a first row 27 of apertures 17 aligned parallel to a first longitudinal edge 41 of the lid 16, and a second row 28 of apertures 17 aligned parallel to a second longitudinal edge 42 of the lid 16. In this manner, the first row 27 of apertures 17 is juxtaposed parallel to the second row 28 of apertures 17.

In a non-limiting exemplary embodiment, the at least one hemodialysis wand 11 includes a first group 11a of hemodialysis wands 11 removably inserted through the first row 27 of apertures 17, respectively, and a second group 11b of hemodialysis wands 11 removably inserted through the second row 28 of apertures 17, respectively. Advantageously, each hemodialysis wand in each of the first group 11a of hemodialysis wands 11 remains spaced apart from each hemodialysis wand of the second group 1 lb of hemodialysis wands 11.

In a non-limiting exemplary embodiment, the front side wall 13a includes a linear slot 33 spanning along an entire longitudinal length 34 of the bottom side wall 13e. Such a linear slot 33 is positioned at a distal edge 48 of the front side wall 13a such that the collection tray 18 reciprocates parallel to the bottom side wall 13e and thereby remains spaced subjacent to the at least one hemodialysis wand 11.

In a non-limiting exemplary embodiment, the collection tray 18 further includes a handle 35 disposed exterior of the cavity 15 when the collection tray 18 is at a fully inserted position within the container 12.

In a non-limiting exemplary embodiment, a plurality of support brackets 50, 51 are affixed to a rear side wall 13c of container 12. Such support brackets 50, 51 receive a fastener or other support member for hanging the holder 10 above a ground surface.

The present disclosure further includes a method of utilizing a hemodialysis wand holder 10 for maintaining hemodialysis wands 11 in a sanitary environment after being used and rinsed with deionized water. Such a method includes the steps of: obtaining a container 12 having a plurality of side walls 13 (e.g., 13a, 13b, 13c, 13d, 13e) configured to form an open top end 14 and a cavity 15 extending downwardly from the open top end 14; obtaining and removably coupling a lid 16 to the open top end 14 wherein the lid 16 has at least one aperture 17 formed therein; and obtaining and removably inserting at least one hemodialysis wand 11 through the at least one aperture 17 such that the at least one hemodialysis wand 11 is suspended above a bottom one 13e of the side walls 13.

The method further includes the steps of: obtaining and adjustably situating a collection tray 18 along the bottom side wall 13e such that the collection tray 18 spans across a major surface area of the bottom side wall 13e; obtaining and removably positioning a fluid-absorbent liner 20 within the collection tray 18 for receiving fluids dripping down from the at least one hemodialysis wand 11 suspended partially within the cavity 15; and removably reciprocating the collection tray 18 along a linear travel path 19 registered transverse to a front one 13a of the side walls 13.

In a non-limiting exemplary embodiment, the holder 10 may be construed as an assembly including a rectangular-shaped container 12 that is suitably sized and shaped for the placement and containment of wands 11 used in hemodialysis after such wands have been rinsed with de-ionized water (e.g., water from which ionic salts have been removed by ion-exchange). Such a container 12 may be produced from a hard, opaque material and can simultaneously accommodate a plurality of dialysis wands 11. The top of the container 12 is effectively covered with a tight fitting lid 16 that has a plurality of annular-shaped apertures 17 monolithically formed therewith, and are aligned in two or more rows. The circumference of each aperture 17 is slightly smaller than the upper section of each hemodialysis wand 11, which is important for ensuring the wands 11 are suspended above the bottom side wall 13e of the container 12, (e.g., above moisture that accumulates dripping off of the wands 11). The distance between the apertures 17 and the fit of the lid 16 also advantageously ensures that individual wands 11 do not touch each other. A handle may be monolithically formed with each end of the lid 16, which is important for facilitating gripping and transporting of the container 12 without contaminating the wands 11.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A hemodialysis wand holder for maintaining hemodialysis wands in a sanitary environment after being used and rinsed with deionized water, said hemodialysis wand holder comprising:
  a container having a plurality of side walls configured to form an open top end and a cavity extending downwardly from said open top end;
  a lid removably coupled to said open top end, said lid having at least one aperture formed therein;
  at least one hemodialysis wand removably inserted through said at least one aperture such that said at least one hemodialysis wand is suspended above a bottom one of said side walls;
  a collection tray adjustably situated along said bottom side wall, said collection tray being removably reciprocated along a linear travel path registered transverse to a front one of said side walls; and
  a fluid-absorbent liner removably positioned within said collection tray for receiving fluids dripping down from said at least one hemodialysis wand suspended partially within said cavity.

2. The hemodialysis wand holder of claim 1, wherein said at least one hemodialysis wand comprises:
  an upper section including a cylindrical portion and a conical portion attached thereto; and
  a lower section engaged with said upper section, said lower section including a linear rod attached to said conical portion and extending away therefrom.

3. The hemodialysis wand holder of claim 2, wherein said linear rod has a distal end seated above said collection tray while said upper section is supported above said lid.

4. The hemodialysis wand holder of claim 1, wherein said at least one aperture comprises:
  a first row of apertures aligned parallel to a first longitudinal edge of said lid; and
  a second row of apertures aligned parallel to a second longitudinal edge of said lid;
  wherein said first row of apertures is juxtaposed parallel to said second row of apertures.

5. The hemodialysis wand holder of claim 4, wherein said at least one hemodialysis wand comprises:
  a first group of hemodialysis wands removably inserted through said first row of apertures, respectively; and
  a second group of hemodialysis wands removably inserted through said second row of apertures, respectively;
  wherein each hemodialysis wand in each of said first group of hemodialysis wands remains spaced apart from each hemodialysis wand of said second group of hemodialysis wands.

6. The hemodialysis wand holder of claim 1, wherein said front side wall comprises: a linear slot spanning along an entire longitudinal length of said bottom side wall, said linear slot being positioned at a distal edge of said front side wall such that said collection tray reciprocates parallel to said bottom side wall and thereby remains spaced subjacent to said at least one hemodialysis wand.

7. The hemodialysis wand holder of claim 1, wherein said collection tray further comprises:
  a handle disposed exterior of said cavity when said collection tray is at a fully inserted position within said container.

8. A hemodialysis wand holder for maintaining hemodialysis wands in a sanitary environment after being used and rinsed with deionized water, said hemodialysis wand holder comprising:
  a container having a plurality of side walls configured to form an open top end and a cavity extending downwardly from said open top end;
  a lid removably coupled to said open top end, said lid having at least one aperture formed therein;
  at least one hemodialysis wand removably inserted through said at least one aperture such that said at least one hemodialysis wand is suspended above a bottom one of said side walls;
  a collection tray adjustably situated along said bottom side wall, said collection tray being removably reciprocated along a linear travel path registered transverse to a front one of said side walls; and
  a fluid-absorbent liner removably positioned within said collection tray for receiving fluids dripping down from said at least one hemodialysis wand suspended partially within said cavity;
  wherein said collection tray spans across a major surface area of said bottom side wall.

9. The hemodialysis wand holder of claim 8, wherein said at least one hemodialysis wand comprises:
  an upper section including a cylindrical portion and a conical portion attached thereto; and
  a lower section engaged with said upper section, said lower section including a linear rod attached to said conical portion and extending away therefrom.

10. The hemodialysis wand holder of claim 9, wherein said linear rod has a distal end seated above said collection tray while said upper section is supported above said lid.

11. The hemodialysis wand holder of claim 8, wherein said at least one aperture comprises:
  a first row of apertures aligned parallel to a first longitudinal edge of said lid; and
  a second row of apertures aligned parallel to a second longitudinal edge of said lid;
  wherein said first row of apertures is juxtaposed parallel to said second row of apertures.

12. The hemodialysis wand holder of claim 11, wherein said at least one hemodialysis wand comprises:
  a first group of hemodialysis wands removably inserted through said first row of apertures, respectively; and
  a second group of hemodialysis wands removably inserted through said second row of apertures, respectively;
  wherein each hemodialysis wand in each of said first group of hemodialysis wands remains spaced apart from each hemodialysis wand of said second group of hemodialysis wands.

13. The hemodialysis wand holder of claim 8, wherein said front side wall comprises: a linear slot spanning along an entire longitudinal length of said bottom side wall, said linear slot being positioned at a distal edge of said front side wall such that said collection tray reciprocates parallel to said bottom side wall and thereby remains spaced subjacent to said at least one hemodialysis wand.

14. The hemodialysis wand holder of claim 8, wherein said collection tray further comprises: a handle disposed exterior of said cavity when said collection tray is at a fully inserted position within said container.

15. A method of utilizing a hemodialysis wand holder for maintaining hemodialysis wands in a sanitary environment after being used and rinsed with deionized water, said method comprising the steps of:

obtaining a container having a plurality of side walls configured to form an open top end and a cavity extending downwardly from said open top end;

obtaining and removably coupling a lid to said open top end, said lid having at least one aperture formed therein;

obtaining and removably inserting at least one hemodialysis wand through said at least one aperture such that said at least one hemodialysis wand is suspended above a bottom one of said side walls;

obtaining and adjustably situating a collection tray along said bottom side wall such that said collection tray spans across a major surface area of said bottom side wall;

obtaining and removably positioning a fluid-absorbent liner within said collection tray for receiving fluids dripping down from said at least one hemodialysis wand suspended partially within said cavity; and removably reciprocating said collection tray along a linear travel path registered transverse to a front one of said side walls.

\* \* \* \* \*